(12) United States Patent
Lalonde et al.

(10) Patent No.: US 8,992,515 B2
(45) Date of Patent: *Mar. 31, 2015

(54) COOLANT INJECTION TUBE

(75) Inventors: Jean-Pierre Lalonde, Candiac (CA);
Marwan Abboud, Pierrefonds (CA);
Teresa Ann Mihalik, NDG (CA);
Jean-Pierre Desmarais, Saint-Lazare (CA); Dan Wittenberger, L'Ile Bizard (CA)

(73) Assignee: Medtronic CryoCath LP, Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/269,493

(22) Filed: Nov. 12, 2008

(65) Prior Publication Data
US 2009/0118723 A1  May 7, 2009

Related U.S. Application Data

(63) Continuation-in-part of application No. 11/129,044, filed on May 13, 2005, now abandoned.

(51) Int. Cl.
| *A61B 18/18* | (2006.01) |
| *A61B 18/02* | (2006.01) |
| *A61B 17/22* | (2006.01) |
| *A61B 18/00* | (2006.01) |

(52) U.S. Cl.
CPC ....... *A61B 18/02* (2013.01); *A61B 2017/22038* (2013.01); *A61B 2017/22051* (2013.01); *A61B 2018/0022* (2013.01); *A61B 2018/0212* (2013.01); *A61B 2018/0262* (2013.01)
USPC ......................................................... 606/21

(58) Field of Classification Search
CPC ..................... A61B 18/02; A61B 2017/22038; A61B 2017/22051; A61B 2018/0022; A61B 2018/0212; A61B 2018/0262
USPC ........ 604/113, 96.01, 528; 606/21, 22, 20, 23
See application file for complete search history.

(56) References Cited

U.S. PATENT DOCUMENTS

| 5,041,089 A | 8/1991 | Mueller et al. |
| 5,421,826 A | 6/1995 | Crocker et al. |
| 5,466,222 A | 11/1995 | Ressemann et al. |
| 5,470,314 A | 11/1995 | Walinsky |
| 5,624,392 A | 4/1997 | Saab |
| 5,649,909 A | 7/1997 | Cornelius |
| 5,779,671 A | 7/1998 | Ressemann et al. |
| 5,782,811 A | 7/1998 | Samson et al. |
| 5,899,898 A | 5/1999 | Arless et al. |
| 5,971,979 A | 10/1999 | Joye et al. |

(Continued)

FOREIGN PATENT DOCUMENTS

| CA | 2314352 A1 | 6/1999 |
| CA | 2443479 A1 | 10/2002 |

(Continued)

*Primary Examiner* — Aarti B Berdichevsky
(74) *Attorney, Agent, or Firm* — Christopher & Weisberg, P.A.

(57) ABSTRACT

A medical device includes a steering element defining a passage for a guide wire. A fluid injection tube defining a proximal and a distal end is also included, wherein a portion of the fluid injection tube is contoured about a portion of the steering element. A plurality of injection ports may be disposed in the portion of the fluid injection tube contoured about the steering element.

8 Claims, 7 Drawing Sheets

(56) References Cited

U.S. PATENT DOCUMENTS

| | | |
|---|---|---|
| 6,190,355 B1 | 2/2001 | Hastings |
| 6,235,019 B1 | 5/2001 | Lehmann et al. |
| 6,283,959 B1 | 9/2001 | Lalonde et al. |
| 6,355,029 B1 * | 3/2002 | Joye et al. ............... 606/21 |
| 6,428,534 B1 | 8/2002 | Joye et al. |
| 6,551,274 B2 * | 4/2003 | Heiner ............... 604/113 |
| 6,623,448 B2 * | 9/2003 | Slater ............... 604/95.01 |
| 6,716,236 B1 | 4/2004 | Tzeng et al. |
| 6,875,209 B2 | 4/2005 | Zvuloni et al. |
| 6,929,639 B2 * | 8/2005 | Lafontaine ............... 606/20 |
| 7,172,589 B2 * | 2/2007 | Lafontaine ............... 606/20 |
| 7,220,257 B1 * | 5/2007 | Lafontaine ............... 606/21 |
| 7,354,434 B2 * | 4/2008 | Zvuloni et al. ............... 606/20 |
| 7,740,627 B2 | 6/2010 | Gammie et al. |
| 8,012,147 B2 | 9/2011 | Lafontaine |
| 2001/0037081 A1 | 11/2001 | Heiner |
| 2002/0049436 A1 | 4/2002 | Zvuloni et al. |
| 2002/0151880 A1 | 10/2002 | Lafontaine |
| 2003/0060762 A1 | 3/2003 | Zvuloni et al. |
| 2003/0060820 A1 * | 3/2003 | Maguire et al. ............... 606/41 |
| 2003/0088240 A1 | 5/2003 | Saadat |
| 2004/0092867 A1 * | 5/2004 | Murray, III ............... 604/103 |
| 2007/0250050 A1 | 10/2007 | Lafontaine |
| 2008/0004644 A1 * | 1/2008 | To et al. ............... 606/159 |

FOREIGN PATENT DOCUMENTS

| | | |
|---|---|---|
| CA | 2666334 A1 | 3/2003 |
| CA | 2607212 A1 | 11/2006 |
| WO | 9852479 A1 | 11/1998 |
| WO | 9927862 A1 | 6/1999 |
| WO | 2004019798 A1 | 3/2004 |
| WO | WO-2004/019798 | 3/2004 |
| WO | 2006124184 A1 | 11/2006 |
| WO | 2009105482 A1 | 8/2009 |

\* cited by examiner

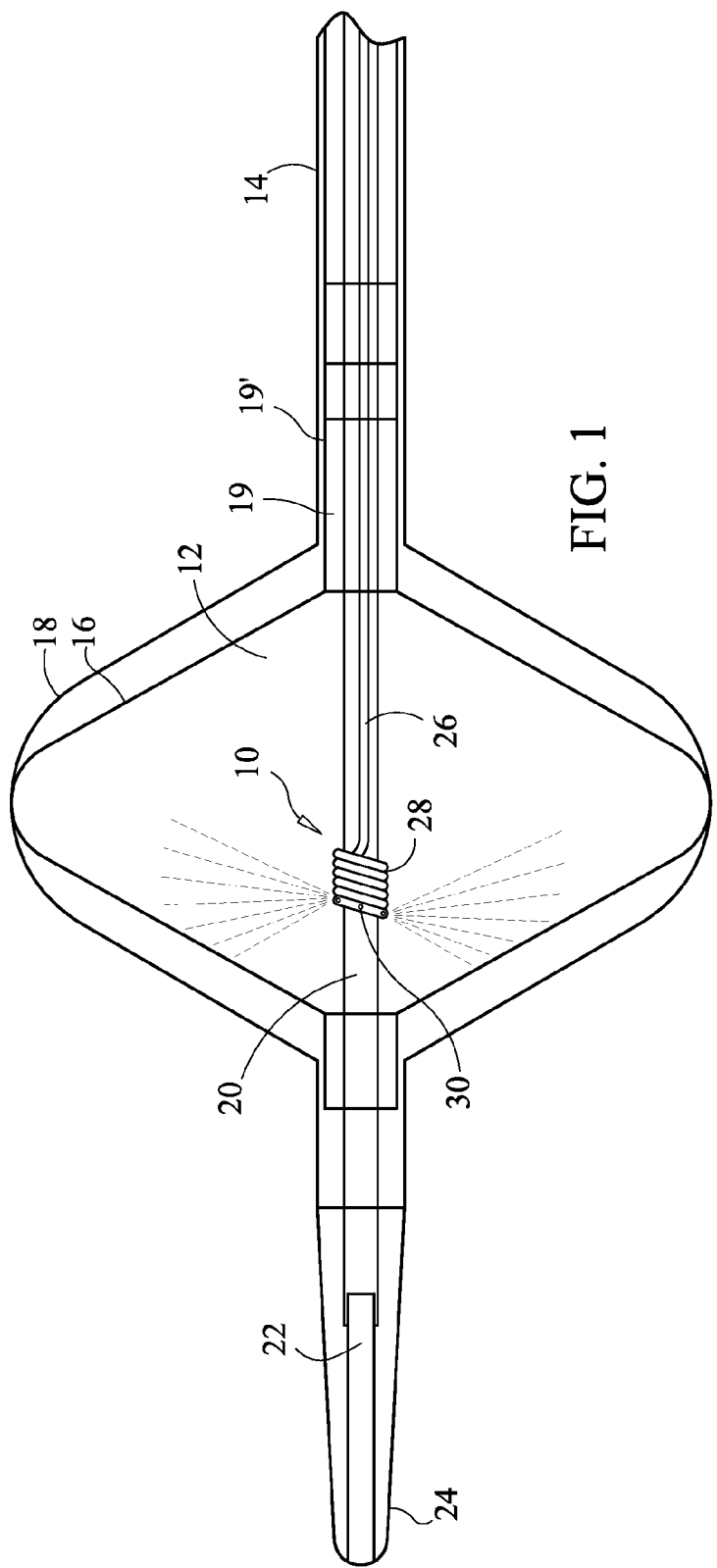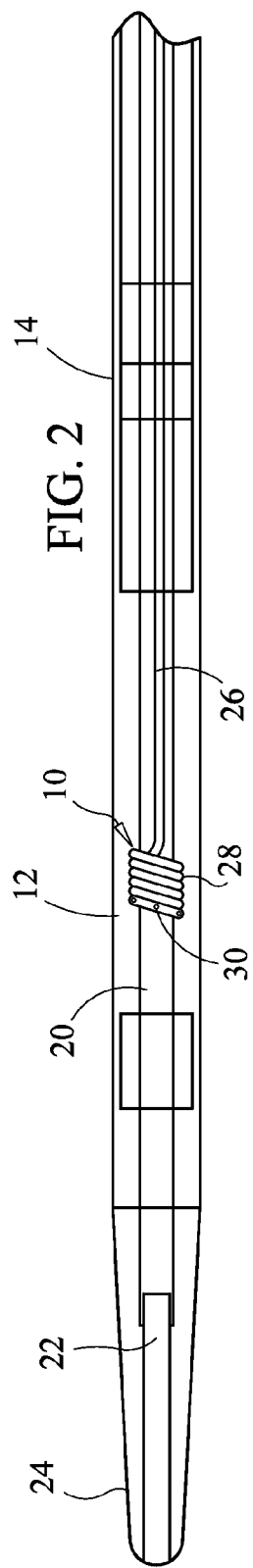

COOLANT INJECTION TUBE

CROSS-REFERENCE TO RELATED APPLICATION

This application is a continuation-in-part of U.S. patent application Ser. No. 11/129,044, filed on May 13, 2005, which is hereby incorporated in its entirety by reference.

STATEMENT REGARDING FEDERALLY SPONSORED RESEARCH OR DEVELOPMENT n/a

FIELD OF THE INVENTION

The present invention relates to a medical device, and more particularly to a coolant injection tube for a thermal treatment medical device.

BACKGROUND OF THE INVENTION

Medical devices are known for thermally treating tissue on the exterior and the interior of the body. One category of such devices is the minimally-invasive, catheter-based device that is introduced into the vasculature. One feature of these devices is the means by which the device is positioned at the treatment site. For example, some devices are actively steered through the vasculature using a steering or deflection mechanism, such as a pull-wire; whereas other devices are introduced over a wire that has already been guided to a selected location, wherein the wire acts as a guide that leads the device to the treatment site. Although a device can be configured so that the guiding wire is substantially external to the device, most known devices include a central longitudinal lumen that receives the wire.

Another feature of the minimally-invasive, catheter-based, thermal-treatment device is the thermal treatment mechanism. One category of devices thermally treats tissue by cooling it, wherein cooling is effected by injecting coolant into a portion of the device, such as a distal device portion that has advantageous thermal transfer properties, and placing the distal device portion near or in contact with the tissue. The distal end portion can have a fixed diameter that is substantially the same as the diameter of the remainder of the catheter or it can have a variable diameter, such as is provided by a balloon. However, regardless of whether the distal end portion is of fixed or variable diameter, the overall size of the device and the injection tube are limited by the dimensions of the vasculature. Typical devices are 2 mm to 4 mm in diameter. Given the small device size, it has proven challenging to cool or freeze warm bodily tissue to a temperature near or well below freezing. Accordingly, it is important to maximize the cooling potential of a particular coolant or refrigerant by delivering or injecting it at a particular location within the device.

In order to cool a treatment segment at a distal end of a device having an expanded or larger surface area than the device body, for example, effective cooling may be achieved by either uniformly spraying or dispersing refrigerant onto the expanded surface of the treatment segment, or by flooding the treatment segment with a refrigerant. Flooding a treatment segment may require larger volumes of coolant, resulting in inefficient use and increased costs, making the substantially uniform spraying or dispersion of coolant an attractive alternative. Devices as depicted in U.S. Pat. No. 6,235,019 provide multiple coolant injection tubes. Alternatively, as shown in U.S. Pat. No. 5,899,898, a single injection tube can be provided with openings along its length. Although such coolant injection structures can be very desirable for creating an elongated cooling zone, they are less suitable for balloon devices or over-the-wire devices. With respect to an over-the-wire device, it will be noted that a relatively large central passage for the wire actually blocks or isolates the injection lying at one side of the passage from the opposite side of the passage, thereby insulating the masked side of the device and creating uneven cooling.

Although not directed to issues related to an over-the-wire device, U.S. Pat. No. 6,551,274 illustrates a loosely coiled injection tube. However, as with the linear injection tubes having a series of longitudinal ports, at regular intervals along the device, the central structure masks the injection tube.

In view of the preceding, it is believed that an improved injection tube would be desirable for use with over-the-wire devices or other devices that have structures other than an injection tube in the cooling chamber of the device.

SUMMARY OF THE INVENTION

The present invention provides for an improved coolant injection tube for use with over-the-wire devices or devices that have structures other than an injection tube in the cooling chamber of the device. For a particular application, a medical device includes a steering element defining a passage for a guide wire. A fluid injection tube defining a proximal and a distal end is also included, wherein a portion of the fluid injection tube is contoured about a portion of the steering element. A plurality of injection ports may be disposed in the portion of the fluid injection tube contoured about the steering element.

For a particular application, the medical device includes a steering element defining a passage for a guide wire. A catheter having a proximal end and a distal end is also included, wherein the catheter defines a lumen, and wherein the passage for the guide wire is disposed within the lumen of the catheter. A first fluid injection tube defining a first proximal and first distal end is included. A second fluid injection tube defining a second proximal and a second distal end may also be included.

The present invention further provides a medical device for thermally affecting tissue including a steering element defining a passage for a guide wire; a fluid injection tube defining a proximal and a distal end, where a portion of the fluid injection tube is contoured about a portion of the steering element; and a plurality of injection ports disposed in the portion of the fluid injection tube contoured about the steering element. The device may further include a substantially cylindrically-shaped dispersion element disposed about a circumference of the steering element, wherein the dispersion element is further disposed proximal to the distal end. The dispersion element may be in fluid communication with the fluid injection tube, and may be slidable or rotatable about the steering element.

The present invention further includes a medical device for thermally affecting tissue, including a steering element defining a passage for a guide wire; a catheter having a proximal end and a distal end, the catheter defining a lumen for the passage of the guide wire; a first fluid injection tube defining a first proximal end and first distal end; and a second fluid injection tube defining a second proximal end and a second distal end.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein:

FIG. 1 is side section view showing the interior of a catheter based medical device in accordance with the invention;

FIG. 2 is a side view of an embodiment of a catheter based medical device constructed in accordance with the principles of the present invention;

DETAILED DESCRIPTION OF THE INVENTION

Figure 3:
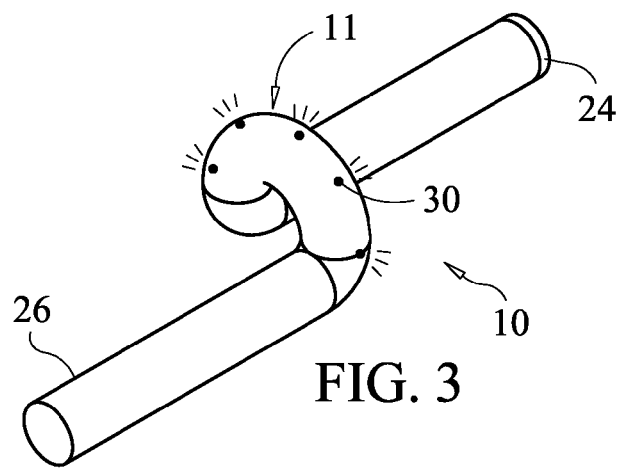
FIG. 3 is a side view of an embodiment of a catheter based medical device constructed in accordance with the principles of the present invention.

Referring to FIGS. 1 and 2, a medical device in accordance with the invention is illustrated. The device includes a fluid injection tube 10 disposed within a lumen 12, space or void defined by a portion of a catheter 14. As shown in FIG. 1, the lumen 12 is defined by a first balloon 16 encapsulated within a second balloon 18. The second balloon 18 contains leaks in the first balloon 16 should they occur and the gap shown between the balloons for the purposes of illustration do not exist when the inner balloon is inflated. Low pressure or vacuum return lumens 19 and 19' are in fluid communication with the interior of the first and second balloons, respectively.

However, referring to FIG. 2, the lumen 12 can also be a substantially uniform diameter passage within a wall portion of the catheter 14, one lumen of a multi-lumen configuration, or central lumen within a catheter that is coaxial with the longitudinal axis of the catheter.

At least a portion of the fluid injection tube 10 is wound around a structure 20 that passes through or is contained within the lumen 12 such as another tube, a wire, a shim, or a spring. In the illustration of FIGS. 1 and 2, the structure 20 may include part of a catheter steering element, namely, a tube that defines a passage 22 or lumen for a guide wire (not shown). As shown, the passage 22 has an open proximal end that is substantially coterminous with the proximal end of the catheter and an open distal end that is substantially coterminous with the distal end of the catheter. The guide wire is suitable for placement into the vasculature of a patient and the passage 22 slides over the wire (i.e., the wire goes through the passage), for guiding the distal portion of the catheter to a desired location using techniques known in the art. The distal end of the catheter can include a soft tip element 24.

Continuing to refer to FIGS. 1 and 2, the fluid injection tube 10 includes a longitudinal portion 26 in fluid communication with a wound portion 28, which may be helical in shape, or shapes that contour around a portion of the passage 22, and wherein the longitudinal portion 26 is disposed adjacent and exterior to the passage 22. In a particular application, the wound portion 28 includes two or more windings (in the illustrated embodiment there are six windings) that span an axial distance along the passage 22 about 0.1 inches. Although the fluid injection tube 10 can be tacked or firmly bonded to the exterior of the passage 22, it can alternatively be secured to the passage 22 only by the encirclement thereof by the wound portion 28 so that the fluid injection tube and the passage can be axially movable with respect to each other.

The fluid injection tube 10 can be apertured or plugged at its distal end, and/or it can include multiple radially-spaced injection ports 30 along wound portion 28. The radially spaced injection ports 30 can be equally spaced apart. For example, four injection ports 30 may be spaced 90° apart on the distal-most winding. The longitudinal portion 26 or the wound portion 28 may be constructed from plastics or metals such as polyimide, stainless steel, nitinol, or the like. The injection ports 20 may be disposed along the injection tube 10 such that fluid flowing into the injection tube 10 at high pressure causes the wound portion 28 to rotate about the structure 20 either in a clockwise or counter-clockwise direction to create substantially a 360° spray distribution. When coolant in liquid, gas, or mixed phase state exits the ports 30 (as shown by a stylized spray pattern), the coolant expands and/or fills the lumen or space 12 and then is evacuated through the return lumen 19 after the cooling process.

In a particular application, the longitudinal portion 26 may include 0.0126" polyimide tubing and wound portion 28 may include a stainless steel coil having one or more straightened or longitudinal segments having a 0.022" outer diameter and a 0.018" inner diameter. There are four or more 0.0025" laser drilled ports in the wound portion 28 that are equally spaced.

Referring now to FIG. 3, the longitudinal portion 26 of the fluid injection tube 10 may define a rounded protuberance or semi-annular shaped portion 11 contoured about the structure 20. The injection tube 10 may further include the soft tip element 24 at its distal end. A plurality of injection ports 30 may be radially disposed about the rounded protuberance or semi-annular shaped portion 11 to provide a particular spray distribution. For example, four injection ports may be included to provide a spray distribution of approximately 360°.

Figure 4:
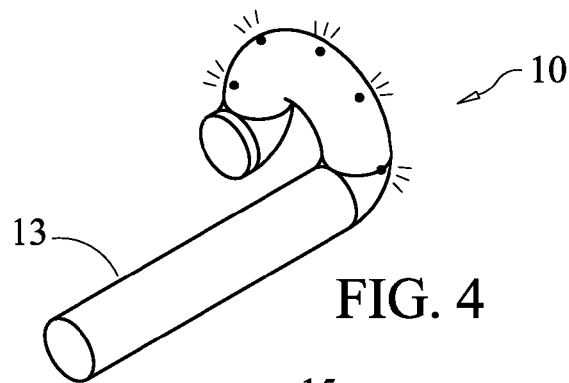
FIG. 4 is a side view of an embodiment of a catheter based medical device constructed in accordance with the principles of the present invention.
Figure 5:
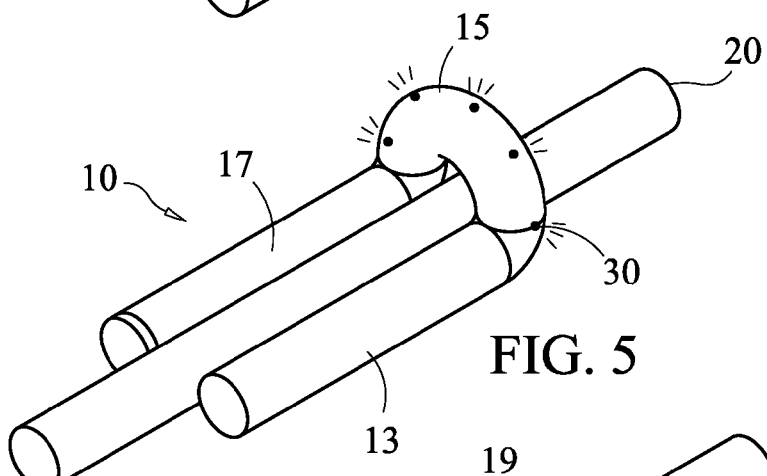
FIG. 5 is a side view of an embodiment of a catheter based medical device constructed in accordance with the principles of the present invention.

Referring now to FIG. 4 and FIG. 5, the longitudinal portion 26 may define a first longitudinal section 13, which may have a contoured portion and a portion substantially parallel to the structure 20. For example, the injection tube 10 may define a curved shaped portion 15 at a distal end of the first longitudinal section 13. The curved shaped portion 15 may be contoured circumferentially about the structure 20. The longitudinal portion 26 may further define a second longitudinal section 17, which may be partially contoured about the circumference of the guide wire lumen 20 and extend proximally substantially parallel to the structure 20. The second longitudinal section 17 may be disposed towards the proximal or distal ends of the structure 20 and may include the soft tip element 24 at its distal end. As shown in FIG. 5, injection ports 30 may be included radially about the curved shaped portion 15. In a particular example, two injection portions or more may be included to provide a desirable spray distribution of approximately 360° around the structure 20.

Figure 6:
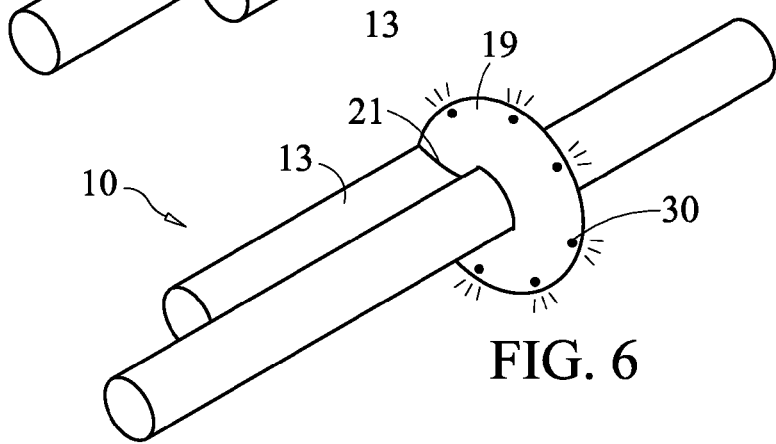
FIG. 6 is a side view of an embodiment of a catheter based medical device constructed in accordance with the principles of the present invention.

Referring now to FIG. 6, the distal end of the first longitudinal section 13 may define an annular or ring shaped portion 19 disposed circumferentially about the structure 20. Injection ports 30 may be included radially about the annular or ring shaped portion 19 to provide a spray distribution of approximate 360°. For example, a fluid flow pathway through the annular or ring shaped portion 19 may be unidirectional, either flowing clockwise or counter clockwise from the first longitudinal section 13 of the injection tube 10. A flow control element 21 may be disposed at the juncture between the first longitudinal section 13 and the annular or ring shaped portion 19 to direct the fluid flow about the annular or ring shaped portion 19. The flow control element 21 may be a moveable flap or a valve that may protrude into the junction to regulate the fluid flow about the annular or ring shaped portion 19. The flow control element 21 may be moveable by actuators (not shown) to direct the fluid flow around the annular or ring shaped portion 19. In a particular example, the fluid flow pathway about the annular or ring shaped portion 19 may be bidirectional, whereby the fluid flow path is bifurcated by the flow control element 21 at the juncture. As a result, a portion of the fluid may flow clockwise while another portion may flow counter clockwise.

Figure 7:
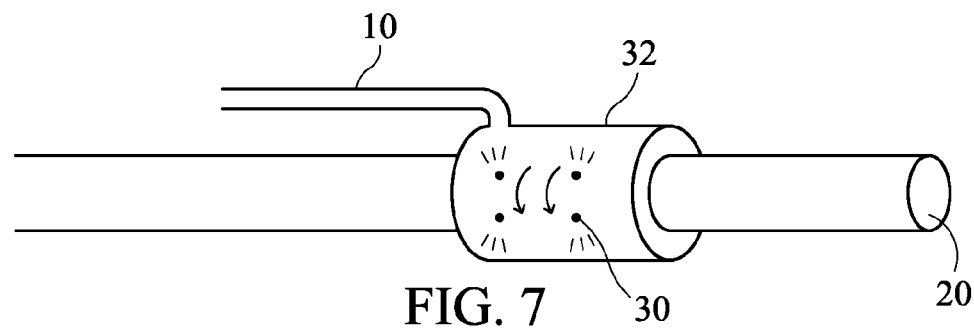
FIG. 7 is a side view of an embodiment of a catheter based medical device constructed in accordance with the principles of the present invention.

Referring now to FIG. 7, fluid may egress from the injection tube 10 into a dispersion element 32, which may be circumferentially disposed about at least a portion of the structure 20. In particular, the dispersion element 32 may include a cylindrical or annular-shaped jacket or collar having one or more flat, concave, or convex faces and a passage therethrough for coupling or placement about the structure. The dispersion element 32 may further be expandable in response to a fluid flow received from the injection tube 10 or alternatively may be a rigid chamber. Injection ports 30 may be included radially about the dispersion element 32 to provide a spray distribution of approximately 360°. For example, as the fluid flows into the dispersion element 32 and out the injection ports 30, the dispersion element 32 may be rotated and/or spun about the structure 20 by centrifugal forces generated from the fluid flow within the dispersion element, thereby providing a dispersive spray distribution about the circumference of the structure 20. The dispersion element 32 may be also be spun by one or more actuators (not shown) disposed within the lumen 12. Alternatively, the dispersion element 32 may be rotated by external rotation of the structure 20.

Continuing to refer to FIG. 7, the dispersion element 32 may include a cylindrically shaped element that surrounds a portion of the structure 20 in a coaxial configuration, for example. The dispersion element 32 may have an inner diameter greater than an outer diameter of the structure 20 such that a space, gap, or offset is present between the two components. A proximal end of the dispersion element 32 may be in fluid communication with or otherwise able to receive fluid flow from the injection tube 10. The proximal junction between the dispersion element 32 and the structure 20 may also be fused, connected, or otherwise sealed such that any fluid directed by the injection tube 10 into the space between the dispersion element 32 and structure 20 cannot flow proximally along the structure 20. Rather, t distal end of the space between the dispersion element 32 and the structure 20 may be open to allow fluid flow to exit the spacing between the two components in a distal direction. In particular, when sufficient coolant flow is delivered by the injection tube 20 to the spacing between the dispersion element 32 and the structure 20, the coolant flow may circulate within the space then exit distally in a conical or frustro-conical shaped distribution pattern having a substantially 360° circumference. Moreover, the angular distribution of the coolant pattern may be predetermined and/or adjusted by tapering a distal end of the dispersion element 32, modifying the dimensions of the space between the dispersion element 32 and the structure 20, or by adjusting the coolant flow rate. For example, a faster coolant flow rate and thus faster rotation of the coolant in the spacing may result in a wider angle distribution upon exiting the space between the dispersion element 32 and structure 20. Further, reduction of the clearance of the space between the dispersion element 32 and structure 20 may result in a wider spray angle.

Figure 8:
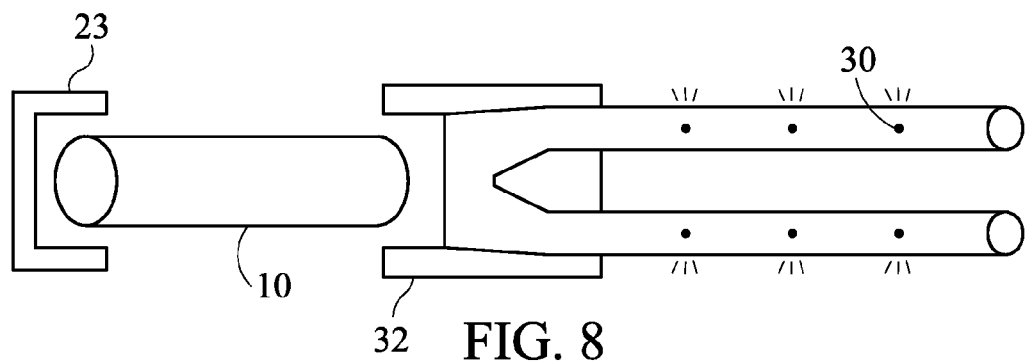
FIG. 8 is a side view of an embodiment of a catheter based medical device constructed in accordance with the principles of the present invention.

Referring now to FIG. 8, a manifold 33 may be disposed about the structure 20 designed to bifurcate the fluid flow from the proximal end of the injection tube 10 into two distal injection tubes. Injection ports 30 may be included on both distal injection tubes to provide a particular spray distribution. A connector 23 may further be provided at the proximal end.

Figure 9:
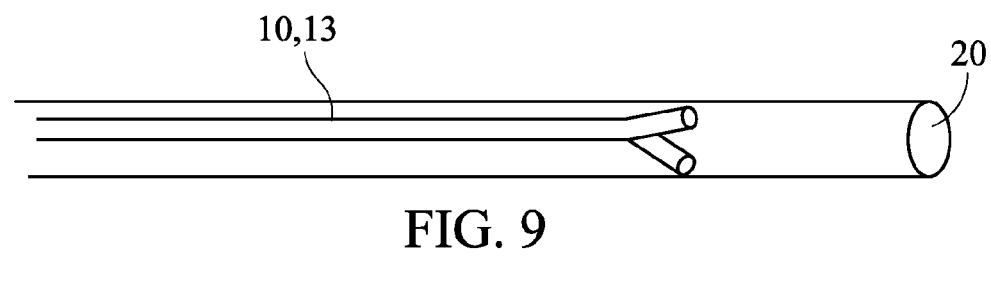
FIG. 9 is a side view of an embodiment of a catheter based medical device constructed in accordance with the principles of the present invention.

Referring now to FIG. 9, the injection tube 10 may be bifurcated at its distal end, wherein the bifurcated distal ends of the injection tube 10 are angled with respect to each other to expel fluid out the distal ends in a particular spray distribution or pattern. For example, the bifurcated distal ends of the injection tube 10 may define approximately a 30° angle with respect to the first longitudinal section 13.

Figure 10:
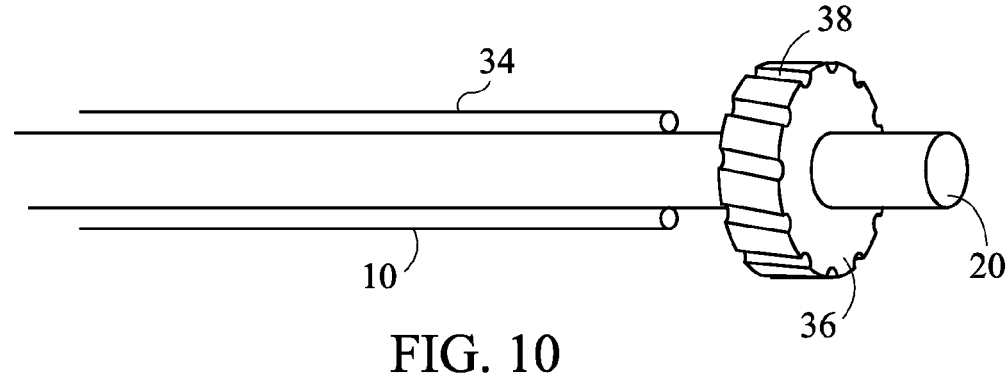
FIG. 10 is a side view of an embodiment of a catheter based medical device constructed in accordance with the principles of the present invention.
Figure 10A:
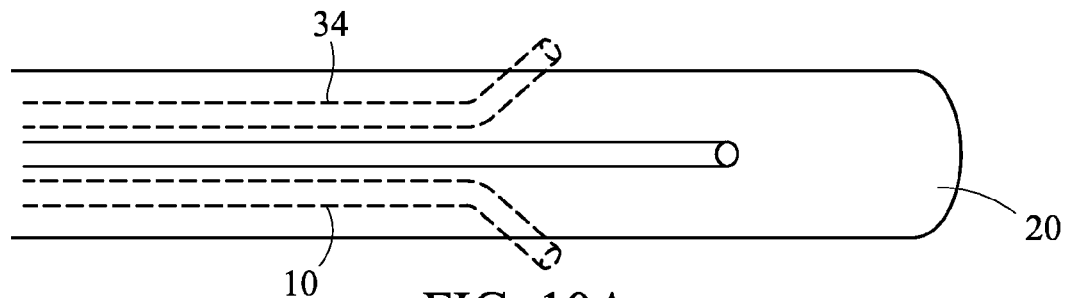
FIG. 10A is an additional illustration of the catheter based medical device of FIG. 9.
Figure 10B:
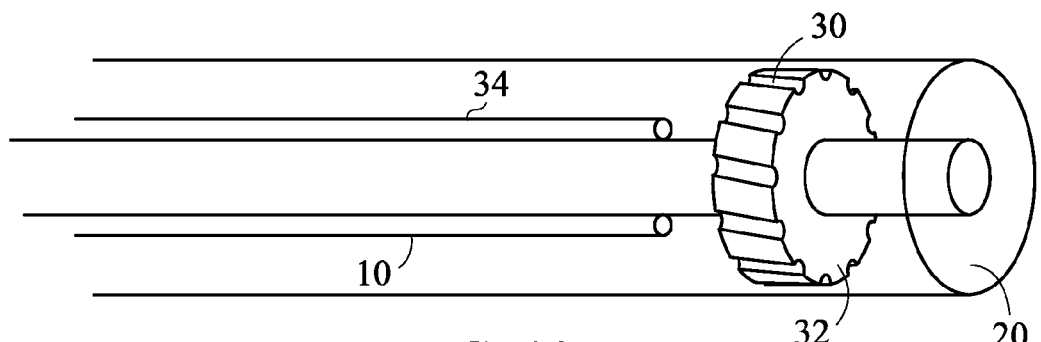
FIG. 10B is an additional illustration of the catheter based medical device of FIG. 7.

Referring now to FIG. 10, a second injection tube 34 may be disposed longitudinally within the lumen 12 about the structure 20. The second injection tube 34 may further be substantially parallel to the injection tube 10. Fluid may egress from the distal ends of the both the injection tube 10 and the second injection tube 34 to provide for a longitudinal spray distribution. As shown in FIG. 10A, the distal ends of the injection tube 10 and the second injection tube 34 may be angled to provide for a particular spray distribution or pattern. As shown in FIG. 10B, fluid may egress from both the injection tube 10 and the second injection tube 34 into the dispersion element 32, which may provide increased fluid flow into the dispersion element 32.

Continuing to refer to FIG. 10, a deflector element 36 may be circumferentially disposed about the structure 20 proximal to both the distal ends of the injection tube 10 and the injection tube 34. The deflector element 36 may be rigid or flexible and may further be movable and slidable along the structure 20. As fluid egresses from the injection tube 10 and/or the second injection tube 34, the fluid may contact the deflector element 36. The deflector element 36 may define one or more slits 38 to direct the fluid flow in a particular direction. The slits 38 may further be angled and slidable along the structure 20 to provide for a particular spray distribution. The slits 38 may all be defined at substantially the same angle, or may be defined at varied angles to provide for a particular spray distribution.

Figure 11:
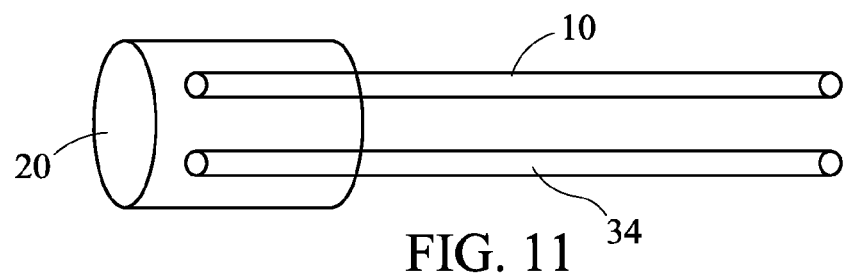
FIG. 11 is a side view of an embodiment of the catheter based medical device.
Figure 12:
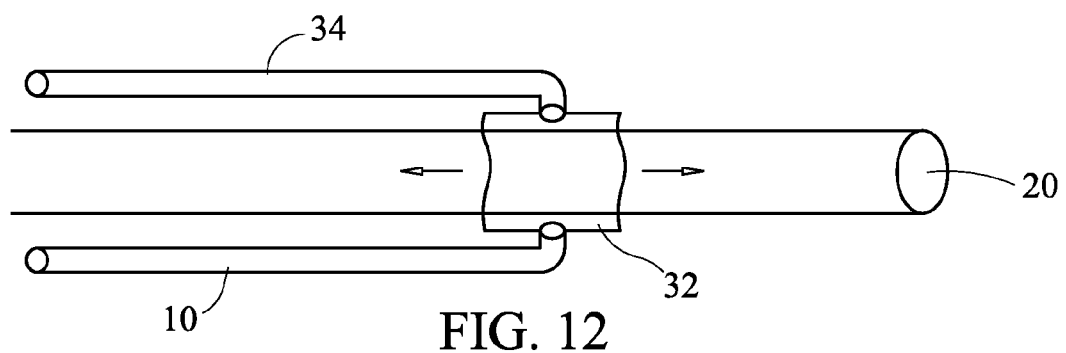
FIG. 12 is a side view of an embodiment of a catheter based medical device constructed in accordance with the principles of the present invention.
Figure 13:
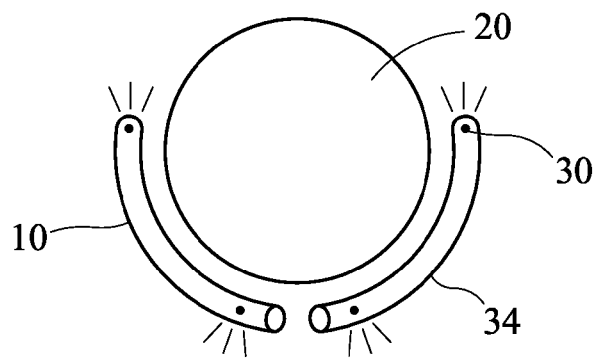
FIG. 13 is a distal end view of an embodiment of a catheter based medical device constructed in accordance with the principles of the present invention.
Figure 14:
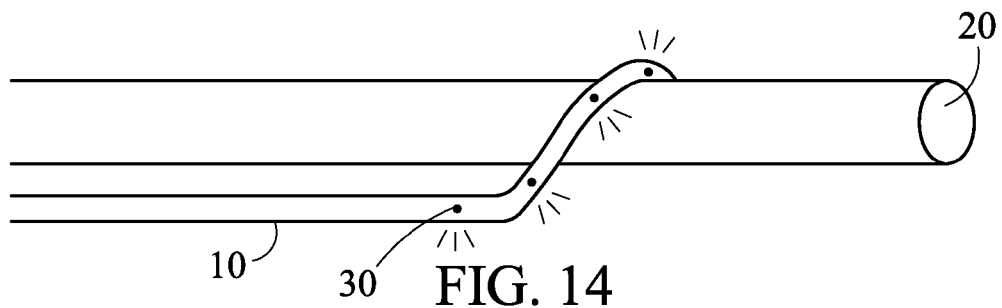
FIG. 14 is a side view of an embodiment of a catheter based medical device constructed in accordance with the principles of the present invention.
Figure 15:
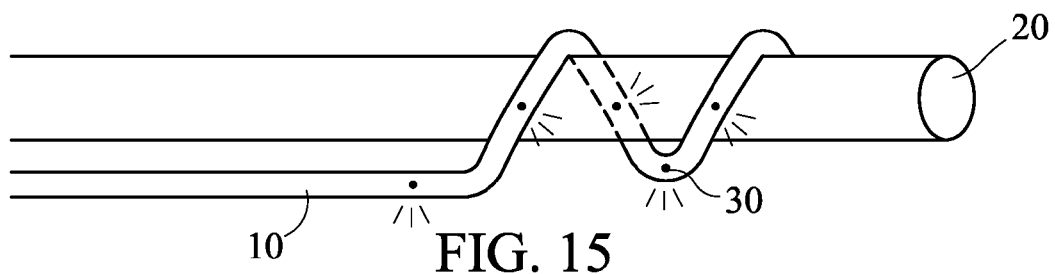
FIG. 15 is a side view of an embodiment of a catheter based medical device constructed in accordance with the principles of the present invention.
Figure 16:
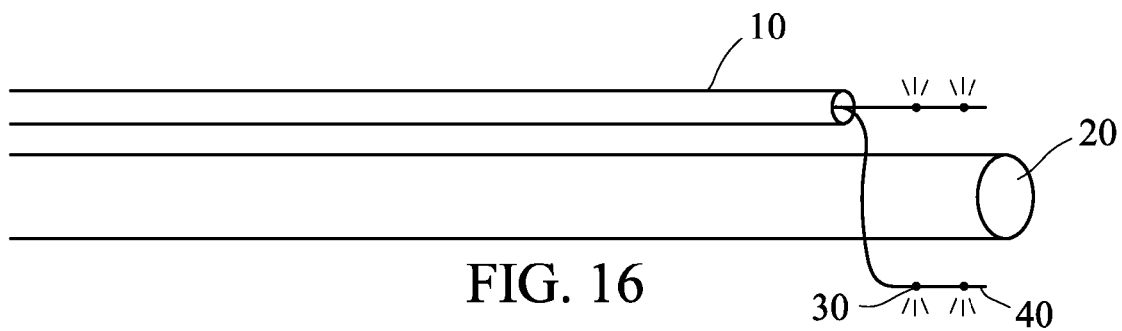
FIG. 16 is a side view of an embodiment of a catheter based medical device constructed in accordance with the principles of the present invention.
Figure 17:
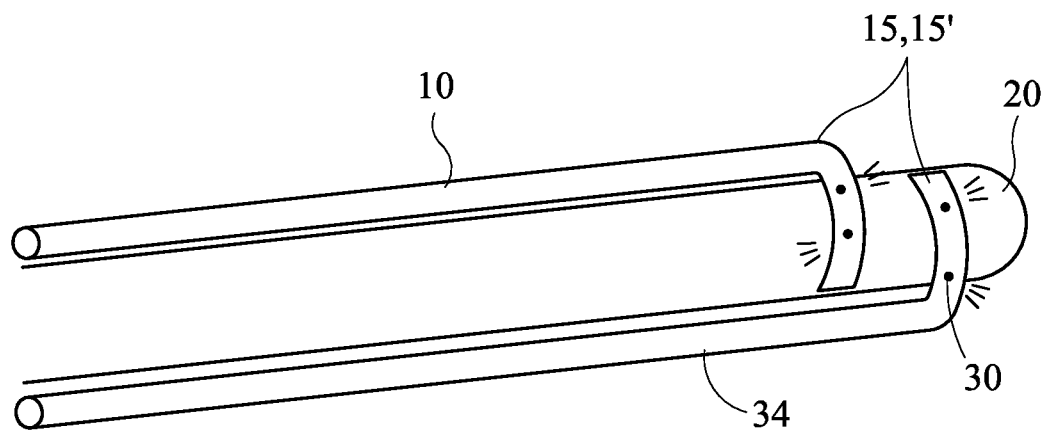
FIG. 17 is a perspective view of a catheter based medical device constructed in accordance with the principles of the present invention.
Figure 18:
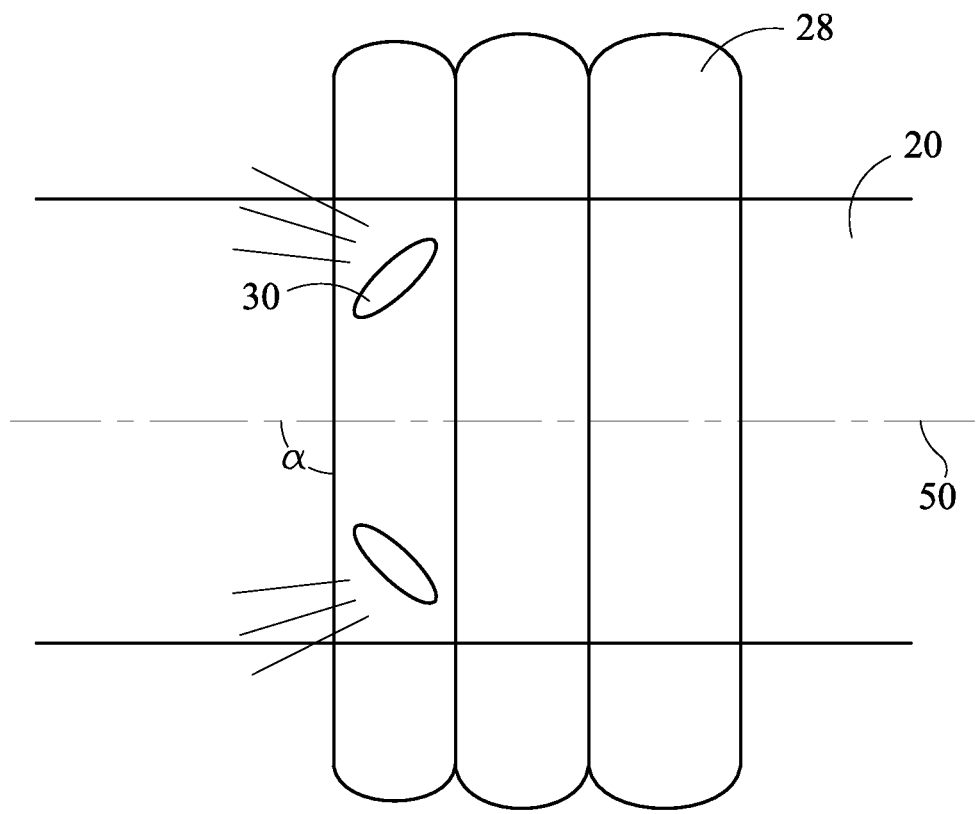
FIG. 18 is side section view showing the interior of an embodiment of a catheter based medical device constructed in accordance with the invention.
Figure 19:
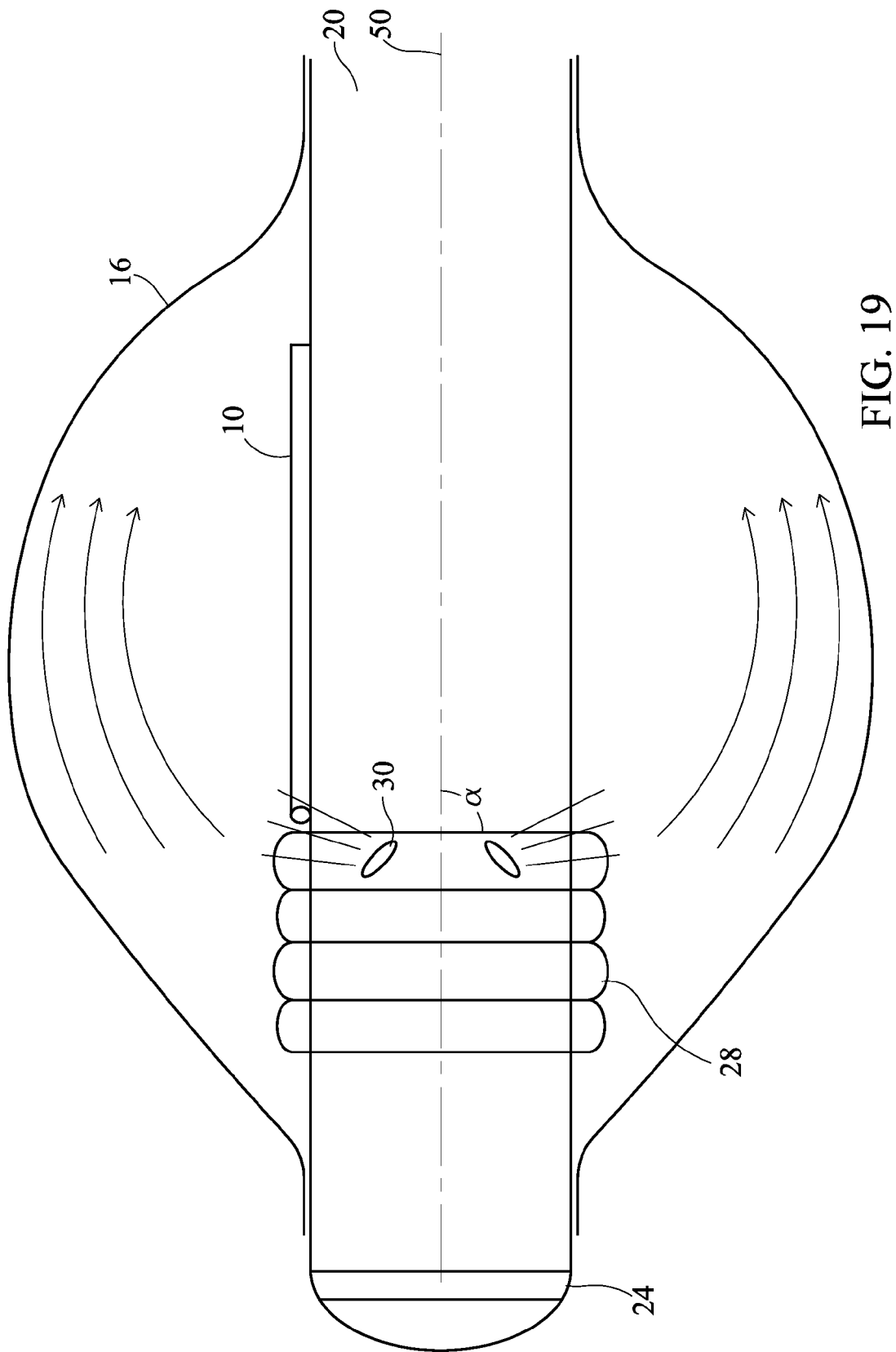
FIG. 19 is side section view showing the interior of an embodiment of a catheter based medical device constructed in accordance with the invention.

Referring now to FIG. 11, in a particular application, the first injection tube 10 and the second injection tube 34 may be disposed within a large injection tube 39. The large injection tube 39 may be disposed about the structure 20 and may extend from the proximal to the distal end of the structure 20. The large injection tube 39 may further contour the structure 20 in a spiral, helical, or other shape, to provide for a particular spray distribution. Fluid may egress from the distal ends of the both the injection tube 10 and the second injection tube 34 to provide for a particular spray distribution.

Referring now to FIG. 12, in a particular application, the dispersion element 32 may be circumferentially and slidably disposed about the structure 20. The dispersion element 32 may be expandable or alternatively a rigid structure sized to receive a desired volume of fluid. Injection ports 30 may be included radially about the dispersion element 32 to provide for a particular spray distribution or pattern. Both the injection tube 10 and the second injection tube 34 may further be in fluid communication with the dispersion element 32. As the volume of fluid in dispersion element 32 increases from the deposited fluid, one or more actuators (not shown) may then operate to slide the sleeve along the structure 20 to a desired location. Further, the dispersion element 32 may be spun and/or rotated to spray fluid into the desired location along the length of the structure 20.

Referring now to FIG. 13, the injection tube 10 may be curved or semi-annular shaped spanning from its proximal end to a point along the structure 20. The injection tube 10 may further contour a part of the circumference of the structure 20 and may be moveable and slidable about the structure 20. As such, fluid may egress from the injection tube 10 providing for a 180° spray distribution. The second injection tube 34 may also be added to cover the remaining 180° spray distribution.

Referring now to FIG. 14 and FIG. 15, in particular applications, the injection tube 10 may be disposed in a spiral contour about the structure 20. The spiraled contour of the injection tube 10 may span from a position proximal the distal end of the injection tube 10 to the distal end of the injection tube (as shown in FIG. 14), or may span from the proximal end to the distal end of the injection tube 10 (as shown in FIG. 15). Injection ports may be included to provide a spiraling spray distribution along the length of the structure 20. The second injection tube may also be added to cover the remaining spray distribution not covered by the first injection tube 10. As fluid flows through the spiral contour, the fluid may egress out each injection port 30 to provide for a 360° spray distribution.

Referring now to FIG. 16, one or more injection tubes 40 having diameters less than the diameter of the injection tube 10 defining proximal and distal ends may be disposed within injection tube 10. The narrow tubes 40 may be deflectable and movable at their distal ends and may be guided to a particular location for fluid distribution. Injection ports 30 may be included at the distal ends narrow injection tubes 40 to provide for a targeted spray distribution. The narrow injection tubes 40 may be guided by one or more actuators (not shown).

Referring now to FIG. 17, the injection tube 10 and the second injection tube 34 may extend longitudinally along the length of the structure 20. For example, the injection tube 10 and the second injection tube 34 may be substantially parallel and disposed approximately 180° apart, wherein each injection tube may be moveable and slidable along the length of the structure 20. The injection tube 10 and the second injection tube 34 may each further define a curved portion 15, 15' at approximately a 90° angle, wherein each respective curved portion 15, 15' is substantially perpendicular to the opposite injection tube. For example, the curved portion 15 defined by the injection tube 10 may be substantially perpendicular to the injection tube 34. The curved portion 15 may radially contour the structure 20 or may be radially suspended just above the structure 20. For example, the curved portions 15, 15' may be suspended above the structure 20 and span part of the circumference of the structure 20 to a position proximal the opposite injection tube. Injection ports 30 may be included radially along each the curved portions 15, 15' to provide a spray distribution of approximately 180. For example, the injection tube 10 and the second injection tube 34 may rotated such that the curved portions 15, 15' on each injection tube cooperate to provide a 360° spray distribution.

Now referring to FIGS. 18 and 19, a side view of a catheter-based medical device is shown where the injection tube 10 is disposed about the structure 20, similar to that shown in FIG. 1. In particular, the injection ports 30 on the wound portion 28 of the injection tube 10 may be disposed at an angle with respect to a longitudinal axis 50 running substantially parallel to the structure 20. For example the injection ports 30, and thus the directed dispersion or direction of coolant spray exiting the injection ports, may have an angle $\alpha$ between approximately 10° and 80° with respect to the longitudinal axis 50. By angling the dispersion of the coolant output from the injection ports, increased coolant efficiency and lower temperatures may be achieved at particular portions of the treatment portions of the device, such as the distal portions of the first and second balloons 16, 18. In addition, as shown in FIG. 19, the wound portion 28 and the injection ports 30 may be positioned towards a distal end or segment of the structure 20, and thus towards a distal segment or portion of the first and second balloons 16, 18. The injection ports may be angled such that coolant dispersion is directed in a proximal direction and towards the vacuum return lumen 19. For example, the injection ports (and their corresponding coolant spray direction) may be at an angle $\alpha$ between approximately 10° and 80° with respect to the longitudinal axis 50. By angling the spray output of the injection ports 30 towards the proximal end of the device, the coolant spray may be more efficiently directed to the balloon surfaces due to the centrifugal force and capillary effect to thereby improve heat transfer between the coolant, the balloon, and any contacting tissue as well as improving the cooling power distribution (i.e., temperature and uniformity) over substantially the entire surface of the balloons.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A medical device for thermally affecting tissue comprising:
   a catheter defining a proximal end, a distal end, and a lumen therein;
   a steering element disposed within the lumen and defining a passage for a guide wire;
   a first fluid injection tube defining a first distal end;
   a second fluid injection tube defining a second distal end;
   a coolant source in communication with first and second fluid injection tubes; and
   a deflector element directing fluid flow from the first and second fluid injection tubes, the deflector element being distally spaced from the first and second distal ends of the fluid injection tubes and defining a substantially cylindrical body defining one or more slits in an outer circumferential surface of its cylindrical body.

2. The medical device of claim 1, wherein the deflector element is disposed circumferentially about the steering element.

3. The medical device of claim 2, wherein the deflector element is slidably positionable about the steering element.

4. The medical device of claim 2, wherein the deflector element is rotatably positionable about the steering element.

5. A medical device for thermally affecting tissue comprising:
   a catheter defining a proximal end, a distal end, and a lumen therein;
   a steering element disposed within the lumen and defining a passage for a guide wire;
   a first fluid injection tube defining a first distal end;
   a second fluid injection tube defining a second distal end; and
   a deflector element distally spaced from the first and second distal ends of the fluid injection tubes, wherein the deflector element defines a substantially cylindrical body defining one or more slits in an outer circumferential surface of its cylindrical body.

6. A medical device for thermally affecting tissue comprising:
   a steering element defining a passage for a guide wire;
   a catheter having a proximal end, a distal end, and a lumen defined therein, wherein the steering element is disposed within the lumen;
   a first fluid injection tube defining a first distal end;
   a second fluid injection tube defining a second distal end;
   a deflector element distally spaced from the first and second distal ends of the fluid injection tubes, the deflector element defining a substantially cylindrical body defining one or more slits in an outer circumferential surface of its cylindrical body; and
   a coolant source in communication with first and second fluid injection tubes, wherein at least one of the first and second distal ends is angled with respect to a longitudinal axis of the steering element.

7. A medical device for thermally affecting tissue comprising:
   a catheter defining a lumen and a longitudinal axis;
   a steering element disposed within the lumen, the steering element defining a passage for a guide wire;
   a fluid injection tube defining a distal portion at least partially coiled around a portion of the steering element, wherein the fluid injection tube is slidable with respect to the steering element; and
   a plurality of outwardly-facing, radially spaced injection ports disposed in the distal portion of the fluid injection tube, each of the plurality of injection ports being oriented at an angle between approximately 10° and approximately 80° with respect to the longitudinal axis of the catheter.

8. The medical device of claim 7, wherein the fluid injection tube is rotatable about the steering element.

* * * * *